(12) United States Patent
Reiderman et al.

(10) Patent No.: US 7,343,192 B2
(45) Date of Patent: Mar. 11, 2008

(54) MAGNETIC RESONANCE IMAGING METHOD AND APPARATUS FOR BODY COMPOSITION ANALYSIS

(75) Inventors: Arcady Reiderman, Houston, TX (US); Gersh Z. Taicher, Houston, TX (US); Zinovy Krugliak, Houston, TX (US)

(73) Assignee: Echo Medical Systems, LLC, Houston, TX (US)

( * ) Notice: Subject to any disclaimer, the term of this patent is extended or adjusted under 35 U.S.C. 154(b) by 605 days.

(21) Appl. No.: 10/669,043

(22) Filed: Sep. 23, 2003

(65) Prior Publication Data
US 2005/0065431 A1 Mar. 24, 2005

(51) Int. Cl.
*A61B 5/05* (2006.01)
(52) U.S. Cl. .................... 600/410; 324/309
(58) Field of Classification Search ............ 600/410, 600/407; 324/309, 313
See application file for complete search history.

(56) References Cited

U.S. PATENT DOCUMENTS

| 4,480,228 | A | * | 10/1984 | Bottomley | 324/309 |
|---|---|---|---|---|---|
| 4,720,679 | A | * | 1/1988 | Patrick et al. | 324/309 |
| 4,784,146 | A | * | 11/1988 | Mancuso et al. | 600/422 |
| 5,194,809 | A | * | 3/1993 | Lew | 324/309 |
| 5,402,787 | A | * | 4/1995 | Van Yperen | 600/410 |
| 5,517,118 | A | * | 5/1996 | Crowley et al. | 324/309 |
| 6,278,891 | B1 | * | 8/2001 | Reiderman et al. | 600/410 |
| 2003/0069497 | A1 | * | 4/2003 | Ochi et al. | 600/422 |

* cited by examiner

*Primary Examiner*—Brian L. Casler
*Assistant Examiner*—Jacqueline Cheng
(74) *Attorney, Agent, or Firm*—Richard A Fagin

(57) ABSTRACT

A method is disclosed for analyzing body composition. The method includes inducing a static magnetic field in the body. The static magnetic field has a known distribution along a longitudinal axis of the body. A radio frequency magnetic field is induced in the body. The radio frequency and a bandwidth thereof are selected to induce nuclear magnetic resonance phenomena in a selected axial segment along the body. Nuclear magnetic resonance phenomena are from the selected axial segment. Composition is determined from the magnetic resonance signals. The measurement may be repeated in different axial segments by changing the static field amplitude or a frequency of the RF magnetic field. In some embodiments, a gradient field is superimposed over the static field.

9 Claims, 9 Drawing Sheets

MAGNETIC RESONANCE IMAGING METHOD AND APPARATUS FOR BODY COMPOSITION ANALYSIS

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The invention is related to the field of Nuclear Magnetic Resonance (NMR) and Magnetic Resonance Imaging (MRI) apparatus and methods. More particularly, the invention relates to apparatus and methods for determining a known component from a mixture of unknown components. More specifically, the invention relates to methods and apparatus for using NMR for precise and quantitative determination of material composition. In one application methods and apparatus according to the invention relate to using NMR for rapid, quantitative in-vivo determination of tissue properties, such as Fat-to-Lean ratio of selected components of an animal and a human body.

2. Background Art

The description of the invention and its background are explained herein in the context of Fat-to-Lean ratio determination of animal and human body components or subsections. It is to be explicitly understood, however, that the invention is not limited to analysis and monitoring of Fat-to-Lean ratio. For example, Fat-to-Lean-to-Bone ratio may also be determined using methods and apparatus according to the invention. Fat composition (different fatty acids), lean composition (water, protein, and glycogen), and bone composition (mineral, collagen, and water) may also be determined using methods and apparatus according to the invention.

In human health monitoring and treatment, the level of total body mass that is derived from adipose mass is the variable that has been determined empirically to be most closely associated with risk for pathology. Advanced models of body composition and newer technologies that precisely and accurately calculate adipose mass may eventually replace simple anthropometric methods such as body weight, height, waist circumference, skin fold thickness, etc. in determining likelihood of pathology.

Body Mass Index (BMI) is defined as body weight (kg)/height$^2$ (m$^2$). Although BMI is a reasonable marker of energy balance for individuals, it is very rough marker of adiposity across populations.

Hydrostatic weighing or Under Water Weighing (UWW) has been the most preferred technique for human whole body composition analysis for several decades. However, due to several practical inconveniences and questionable underlying assumption its usage is limited. UWW assess whole body fat content expressed as a percentage of body weight. See, for example, U.S. Pat. No. 4,873,866 to Fairbanks.

UWW based on a two-component (2C) body composition model assumes specific densities 0.9 and 1.1 g/cm$^3$ for Fat Mass (FM) and Fat-Free Mass (FFM) respectively. UWW further assumes that these densities are constant within different individuals or populations. Whole body densities have been determined to vary in a range between 1.08 g/cm$^3$ (very lean) and 1.00 g/cm$^3$ (severely obese).

Other UWW techniques are based on four-component (4C) or three-component (3C) body composition models. 4C and 3C models additionally use assumptions that FFM is composed of constant proportions of water (73.2%), minerals (6.8%), and protein (19.5%) each having a specific density assumed to be constant at body temperature. Precise measurement of Total Body Water (TBW) and Bone Mineral Content (BMC) are required to use 4C and 3C models because of the potential for additional error in the final results for FM that is related to TBW and BMC measurements. In certain human population groups, such as children, the elderly, African-Americans, or sick patients, 4C or 3C methods may provide more accurate estimates of FM than the 2C method.

UWW is not practical for accurate measurements in individuals having cardiovascular or pulmonary disorders, elderly, young children, and very obese subjects. Substantial errors may occur due to body movement and the buoyant effects of air in the gastrointestinal tract and lungs. The simultaneous measurement of residual lung volume and underwater weight may be preferred because it controls for the effects of the increased pressure of water on the thorax during immersion. Inaccurate measurements of air in the lungs can be a major source of error when estimating body density from underwater weighing. However, UWW may be the only practical method of measuring body fat in very obese subjects who cannot be evaluated by other methods.

U.S. Pat. No. 4,144,763 to Vogelman and U.S. Pat. No. 5,105,825 to Dempster disclose plethysmography apparatuses and methods. Plethysmography is a more convenient way for measuring body adiposity as compared to UWW. Measurement of body density by plethysmography allows for a high degree of precision in volume measurement, but inconsistencies in body density, the necessity for lung volume correction, variation in skeletal mass, and degree of hydration are not accounted for by plethysmography methods.

U.S. Pat. No. 6,393,317 to Fukuda et al. and U.S. Pat. No. 5,415,176 to Sato et al. disclose two examples of widely used techniques for fat assessment based on body bioelectrical impedance. A method for fat assessment based on body electrical conductivity is described by Unangst E. T., Jr., and Merkley L. A. in, *The effects of lipid location on non-invasive estimates of body composition using EM-SCAN technology*, J. Exp. Biol., 2002:205 (Pt. 19) pp. 3101-3105.

None of the foregoing methods of body composition analysis have been broadly implemented, largely because of inaccuracy and poor specificity of the results. Measurement of body composition of experimental animals by plethysmography, hydrostatic weighing (UWW), bioelectrical impedance, and electrical conductivity has not proven to be practical.

In order to provide a more precise quantitative measure of whole body composition in animals, the Dual Energy X-ray Absorptiometry (DEXA) technique is more widely used than the foregoing techniques. U.S. Pat. No. 6,233,473 to Shepherd et al. discloses a method of body composition analysis using a dual-energy, fan-shaped distribution of X-rays, and detector signal processing that corrects for mass magnification and other effects due to the geometry of the measurement system. In the method disclosed in the '473 patent, the thickness of the attenuating material along respective ray paths is obtained by using a four-dimensional look-up table derived experimentally from step-wedge measurements, and another look-up table and interpolation between table entries are used to convert projected mass to true mass.

DEXA precision differs with the instrument type, the particular animal species being evaluated, the software and the actual methods that are used. The basic physical principle of DEXA is associated with attenuation of X-rays transmitted through an object. The degree of attenuation (attenuation coefficient) depends on the object's thickness, density, and chemical composition as well as the initial energy of the X-ray photons. At low initial photon energies (less than about 0.8 million electron volts), photon attenuation is non-linear, and is governed by the photoelectric effect and by Compton scattering. If the object under evaluation is composed of two or more homogeneous materials, then the composite attenuation coefficient may be approximated by a weighted sum of the individual attenuation coefficients, each weighted for its fractional contribution to the total mass.

The attenuation of X-rays through lean human body tissue and fat tissue is slightly different, but is substantially different for bone tissue, primarily because of their differences in density and chemical composition. DEXA does not provide three independent measurements, even though three body composition values: bone; lean; and fat tissue fractional amounts are reported. With increasing initial photon energy, the differences in the attenuation properties for these three types of body tissue decrease.

The following is summary of a DEXA technique for whole body composition analysis of laboratory mice. First, a record is made of the attenuation of X-rays at both initial photon energy values in air. Then the pixel size, scanning speed and beam size are selected. A scan of the object (mouse) is then made. The detected X-ray photon amplitudes and count rates are corrected for detector dead time loss, spill-over from one energy window to another, and for beam hardening. From two equations (two photon energy levels) the amount of soft tissue and bone mineral is then determined.

Soft tissue in the non-bone pixels is separated into fat and lean mass by means of a calibration that translates attenuation coefficients into fat fractions. Corrections are made for tissue thickness variation. The fat content of the soft tissue layer overlying, underlying and/or inside bone is estimated based on predetermined relationships between fat-to-lean ratio of pure soft tissue surrounding bone.

The main advantage of DEXA is the ability to analyze individual regions within an entire body. DEXA as a method for analyzing whole body composition may be subject to the following limitations. First is the assumption that the composition of the soft tissue layer overlying bone has the same Fat-to-Lean ratio, or the ratio is related in a predetermined way to the Fat-to-Lean ratio of other non-bone tissues. For a whole body scan, about 40% of the pixels are typically classified as containing bone. Next, thicker tissue regions remove more low energy photons from the radiation beam as compared to thinner regions, this effect being known as "beam hardening." Further, DEXA assumes homogeneous hydration of lean tissues.

In the field of in-vivo analysis of body composition parameters there have been numerous attempts to use Nuclear Magnetic Resonance (NMR) methods and apparatus. Briefly, these techniques and their limitations are as follows.

I. Magnetic Resonance Spectroscopy (MRS). The MRS method used to quantify fat content in a body is based on recording a $^1H$ (proton) spectrum in-vivo. An example of using a standard MRS apparatus for such analysis is described by Mystkowski et al. in, *Validation of whole-body magnetic resonance spectroscopy as a tool to assess murine body composition*", Int. J. of Obesity, 2000:24, pp. 719-724. A drawback to the technique disclosed in the Mystkowski et al. paper is the fact that many human tissue types contain a variety of lipids which yield $^1H$ spectral peaks within a very narrow chemical shift range. In addition, MRS requires very high homogeneity and strength of the static magnetic field, due to the required high spectral resolution of chemical shifts, making MRS equipment that would be used for whole body composition analysis extremely expensive.

II. Magnetic Resonance Imaging (MRI). A MRI method for body composition analysis is described by Ross et al. in, *Quantification of adipose tissue by MRI: relationship with anthropometric variables*, J. Appl. Physiol. 1992:72(2) pp. 787-795, and in U.S. Pat. Nos. 5,225,781; 5,594,336; 6,147, 492; and 5,644,232. Another MRI technique is described in Thomas et al., *Magnetic Resonance Imaging of Total Body Fat*, J. Appl. Physiol. 85(5):1778-1785 (1998). MRI techniques known in the art for determining body fat and/or body composition analysis make use of conventional MRI systems otherwise adapted for generating visual representations of the internal structure of the body. While effective, such techniques represent a less than efficient use of large, expensive MRI equipment. In particular, MRI techniques known in the art, which use frequency domain analysis of NMR signals acquired over a wide range of frequencies, require large, expensive magnets to induce a highly homogeneous static magnetic field in the body being analyzed. Additionally, live subjects for whole body composition analysis must be sedated, anesthetized, or rendered immobile for substantially long time periods. These are unacceptable requirements, particularly for human infants.

III. NMR Relaxometry. NMR relaxometry methods known in the art avoid the necessity for complicated and expensive equipment. NMR relaxometry methods known in the art, however, have several limitations, such as with respect to accuracy and precision. Kamman et al., *Multi-exponential relaxation analysis with MR imaging and NMR spectroscopy using fat-water systems*, Magn. Reson. Imaging 1987:5(5) pp. 381-392 describes a NMR relaxometry method for body composition analysis. Despite extensive research and development into methods of whole body composition analysis, there is still a need for reliable, accurate, precise, and specific non-invasive methods for acquiring information relating to body fat mass, lean mass, total water content, etc.

In some instances, it is desirable to be able to analyze composition of an animal (or human) body with respect to selected portions of the body, such as the head, abdomen, legs, etc. Additionally, there is a need for body composition analysis of entire bodies, some of which may be longitudinally extensive. As explained above, MRI systems known in the art are capable of performing such apportioned analysis, but represent a less than efficient use of such systems. Accordingly, there is a need for a relatively inexpensive, fast, easy to use system and method for analyzing composition of a body that can analyze selected portions of the body.

SUMMARY OF THE INVENTION

One aspect of the invention is a method for analyzing composition of a body portion. The method includes determining a size and a position of the body portion by imaging a nuclear magnetic resonance parameter of a body in at least one dimension. A static magnetic field and a gradient magnetic field are induced in at least the body portion. A radio frequency magnetic field is induced in at least the body portion at a frequency selected to excite nuclear magnetic resonance phenomena. Nuclear magnetic resonance signals are then detected from at least the body portion. The static magnetic field and the gradient magnetic field have amplitudes selected such that the nuclear magnetic resonance phenomena are induced and detected substantially entirely within the body part.

Another aspect of the invention is a system for body portion composition analysis. A system according to this aspect of the invention includes a magnet for inducing a static magnetic field in a body, a means for inducing radio frequency magnetic fields in the body, a means for detecting nuclear magnetic resonance phenomena in the body, a means for applying a selected amplitude gradient magnetic field to the body and a means for selectively controlling amplitude of the static magnetic field in the body. The means for applying the gradient field and controlling amplitude are configured to image a nuclear magnetic resonance property of the body in at least one dimension at a selected radio frequency. The means for applying the gradient field and means for controlling amplitude are configured to cause excitation of nuclear magnetic resonance phenomena in a portion of the body having a selected position and size. The size is smaller than a size of the body.

Another aspect of the invention is a method for analyzing body composition. A method according to this aspect of the invention includes inducing a static magnetic field in the body, the static magnetic field having a known distribution along a longitudinal axis of the body. A radio frequency magnetic field is induced in the body. The radio frequency field has frequency and a bandwidth selected to induce nuclear magnetic resonance phenomena in a selected axial segment along the body. Nuclear magnetic resonance phenomena are detected from the selected axial segment. The inducing the radio frequency magnetic field and the detecting nuclear magnetic resonance signals are repeated in a different selected axial segment by at least one of applying a selected additional static magnetic field to the body and changing the radio frequency.

Another aspect of the invention is a method for analyzing composition of a body. A method according to this aspect of the invention includes inducing a static magnetic field along a selected axial segment of the body. The static magnetic field is substantially homogeneous in a direction perpendicular to a longitudinal axis of the body and has a known amplitude distribution along the longitudinal axis A radio frequency magnetic field is induced in the selected axial segment. The radio frequency magnetic field is substantially perpendicular to the static magnetic field and is substantially homogeneous along the longitudinal axis at a known position. A frequency and bandwidth of the radio frequency magnetic field are selected to induce nuclear magnetic resonance phenomena in the known position. Nuclear magnetic resonance signals are detected from the known position. The static magnetic field and the radio frequency magnetic field are moved along the longitudinal axis such that the known position is in a different axial portion of the body. The inducing the static magnetic field, the inducing the radio frequency magnetic field and the detecting are then repeated.

Other aspects and advantages of the invention will be apparent from the following description and the appended claims.

DETAILED DESCRIPTION

Systems and methods according to the invention perform one of two general techniques of body composition analysis. Each technique includes some form of localization of nuclear magnetic resonance measurement to within a selected portion of the body being analyzed, and subsequent composition analysis of the body portion from the nuclear magnetic resonance measurements so localized. In one technique, the body is first imaged in one dimension with respect to a nuclear magnetic resonance property to determine the location of selected body components, such as the head, torso, legs, abdomen, etc. Next, nuclear magnetic resonance measurements are made within one or more of the selected body portions by localizing the nuclear magnetic resonance signal excitation and detection to within the one or more selected body components. Finally, the composition of the one or more selected body components is determined from the nuclear magnetic resonance measurements.

In another technique, nuclear magnetic resonance measurements are localized to selected volumes or slices along one dimension of the body. Nuclear magnetic resonance measurements are then made within one or more of the selected volumes, and composition of the selected volumes are then determined using the nuclear magnetic resonance measurements thus made.

Figure 1:
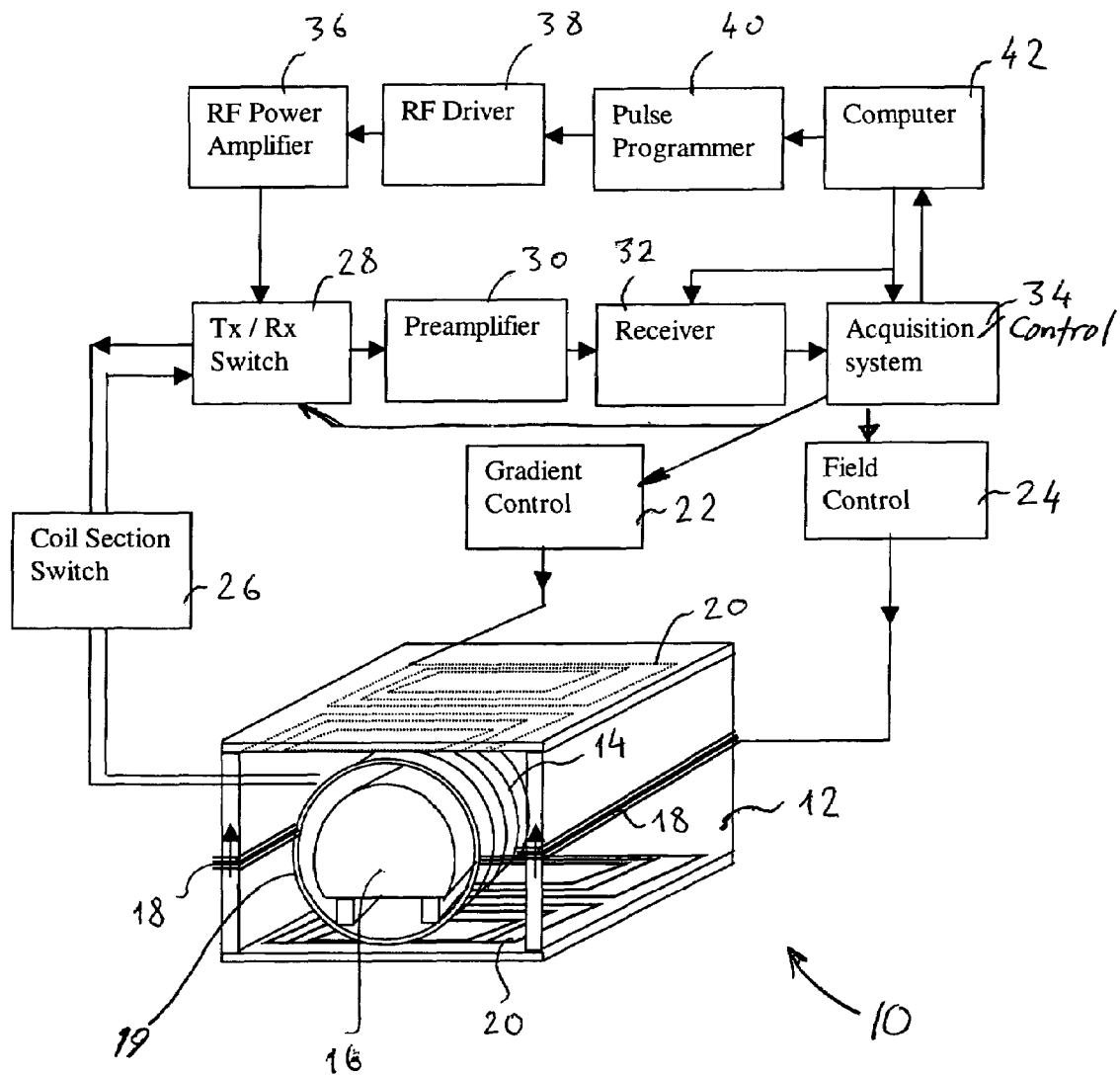
FIG. 1 is a functional block diagram of one embodiment of an apparatus according to the invention.

One embodiment of a nuclear magnetic resonance (NMR) apparatus according to the invention is shown generally in FIG. 1 at 10. The apparatus 10 includes a magnet 12 disposed around or on opposed sides of a sample chamber 16. The magnet 12 may be a permanent magnet, or an electromagnet, and is configured to induce a substantially homogeneous static magnetic field within the sample chamber 16. The sample chamber 16 may be defined by an enclosure such as a polycarbonate tube or box, shown generally at 19 in FIG. 1. The enclosure 19 may be made from any substantially electrically non-conductive and non-ferromagnetic material known in the art, polycarbonate being one example of such materials. As will be explained below with reference to FIG. 3, the magnet 12 need not provide a very high degree of homogeneity in the static magnetic field induced within the chamber 16. It is only necessary that any gradients in the static magnetic field within the chamber 16 be much less in magnitude than applied gradients that are induced by a gradient coil 20, the function of which will be explained below in more detail. In the embodiment shown in FIG. 1, the chamber 16 is a separate enclosure adapted to be easily inserted into and withdrawn from the enclosure 19, but other embodiments may use only the enclosure 19.

A radio frequency (RF) antenna 14 is disposed about the enclosure 19, typically on the exterior surface of the enclosure 19. In the present embodiment, the antenna 14 comprises a wire coil wound so that its turns lie in planes substantially perpendicular to the longitudinal axis of the chamber 16 and the enclosure 19. When pulses of RF electrical power are passed through the antenna 14, an RF magnetic field is induced within the chamber 16. Although described above in terms of coils, the antenna 14 can be configured in any other way as long as the RF magnetic field induced by the antenna 14 is substantially perpendicular to the static magnetic field induced by the magnet 12 within the volume defined by the enclosure 19. The RF magnetic field induces nuclear magnetic resonance phenomena in an object (not shown) disposed in the chamber 16, which phenomena themselves emit radio frequency energy detectable by the same antenna or a different RF antenna (not shown in FIG. 1) disposed near the chamber 16.

In the present embodiment, the antenna 14 performs both RF transmit and RF receive functions, and is coupled, through a coil section switch 26, which will be further explained with reference to FIG. 2, to a Tx/Rx matching circuit and switch ("Tx/Rx switch") 28. The Tx/Rx switch 28 is under control of an acquisition and control system 34 or similar programmable controller configured to operate the Tx/Rx switch 28 such that the antenna 14 is selectively coupled to an RF power amplifier 36 during RF pulse transmission intervals, or to a receiver preamplifier 30 during NMR signal detection (receive) intervals. The input of the RF power amplifier 36 is coupled to the output of an RF driver 38. The input of the RF driver 38 is itself coupled to a pulse programmer 40. The pulse programmer 40 may be a separate element under control of a computer 42, or may be a function performed by the computer 42 itself.

The receiver preamplifier 30 output is coupled to the input of an RF receiver 32, the output of which is coupled to the acquisition and control system 34. The acquisition system 34 may include such circuits as analog to digital converters, digital filters and a recording device (not shown separately). The output of the acquisition and control system 34 is coupled to the computer 42 for analysis of voltages detected by the antenna 14 resulting from NMR phenomena in an object or body (not shown in FIG. 1) disposed in the chamber 16. The foregoing circuit elements, including the acquisition and control system 34, receiver preamplifier 30, Tx/Rx switch 28, computer 42, pulse programmer 40, RF driver 38 and RF power amplifier 36 can be of any type known in the art for generating, detecting and analyzing nuclear magnetic resonance signals.

The pulse programmer 40 is configured to operate the RF driver 38 to cause generation of a succession of selected length and selected frequency RF pulses through the antenna 14, such that NMR phenomena are induced in the object (not shown) disposed in the chamber 16. As is well known in the art, the frequency, amplitude and duration of the RF pulses are related to the amplitude distribution of the static magnetic field within the chamber 16, and to the gyromagnetic ratio of nuclei which are excited within the object (not shown) for NMR relaxometry analysis. For analysis of human and other animal bodies, the nuclei are typically hydrogen ($^1$H).

The system 10 shown in FIG. 1 also includes the previously mentioned gradient coil 20 disposed outside the enclosure 19. The gradient coil 20 is configured such that when direct current (DC) of a selected magnitude is passed through the gradient coil 20, a known gradient magnetic field is superimposed on the static magnetic field induced by the magnet 12. In the present embodiment, the gradient is substantially linear and is directed along the longitudinal axis of the chamber 16. The amount of DC applied to the gradient coil 20 is controlled by gradient control 22, itself under operative control of the acquisition and control system 34.

The system 10 also includes a static field amplitude control coil 18 disposed outside the enclosure 19 and configured to induce a substantially homogeneous static magnetic field that is directionally aligned with the static magnetic field induced by the magnet 12. An amount of DC passed through the field control coil 18 determines an amount of change in static magnetic field amplitude within the chamber 16. The amount of DC is controlled by a field control 24, which is also under operative control of the acquisition and control system 34. A system as shown generally in FIG. 1 can be configured to operate according to one or more aspects of the invention as will be further explained below.

Figure 2:
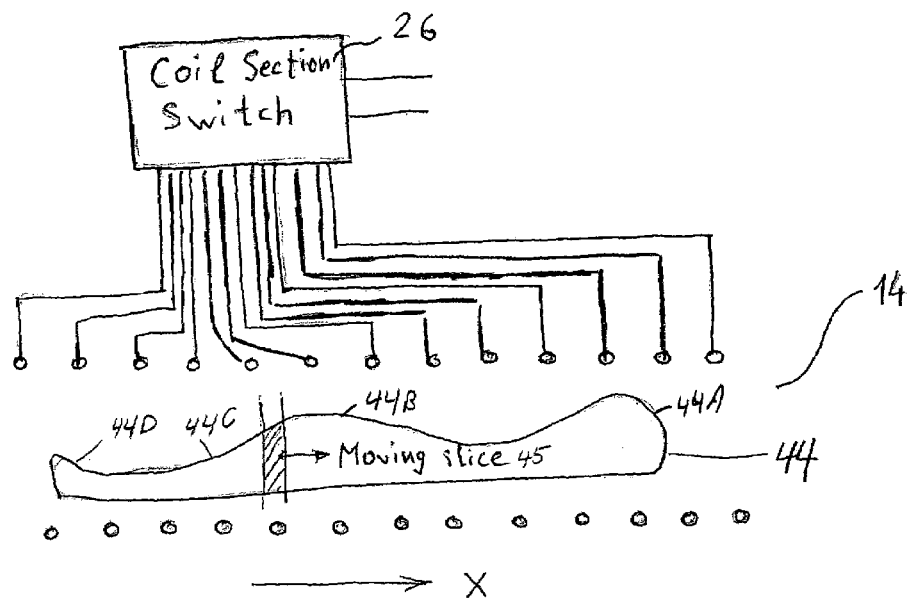
FIG. 2 shows an example one-dimensional NMR imaging technique according to the invention.

Referring to FIG. 2, one function of the coil section switch 26 will now be explained. In methods according to one aspect of the invention, a part of a body 44 to be analyzed can have only a selected portion thereof subjected to RF nuclear magnetization to reduce the amount of NMR energy originating in parts of the body 44 not being analyzed. In the example shown in FIG. 2, the body 44 can be a human infant, disposed generally longitudinally along the chamber (16 in FIG. 1), and showing, generally, head portion 44A, abdominal portion 44B, leg portion 44C and feet portion 44D. The body portions 44A-44D shown in FIG. 2 are only meant as examples. Methods and systems according to the invention are not limited in scope to analysis of the particular example body portions, but may analyze body portions to any degree of size believed to be useful in pathology analysis and prediction. Other embodiments may analyze selected thickness axial "slices" each in a particular position along the axis of the body, as will be further explained below. Irrespective of the size of the body portion being analyzed, the coil section switch 26 can be configured to apply RF power to, and to detect signals from, only the sections of the antenna 14 coil that are disposed near the particular selected body portion being analyzed.

1. One Dimensional Imaging to Determine Position of and Analyze Composition of Selected Portions of a Body.

Figure 3:
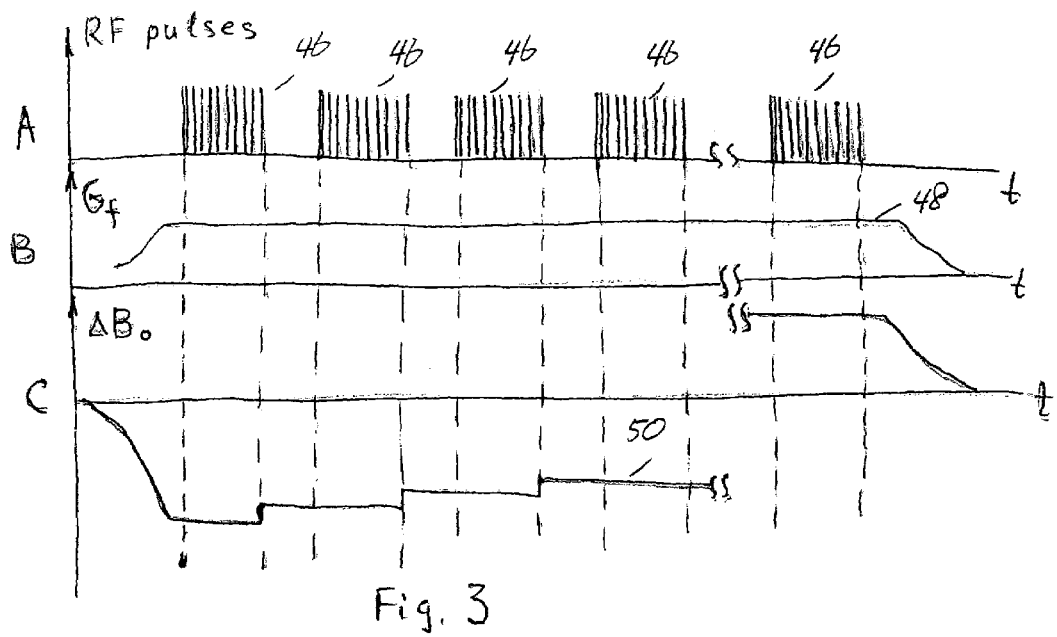
FIG. 3 shows radio frequency magnetic field amplitude, gradient magnetic field amplitude and static magnetic field amplitude with respect to time in an example imaging technique according to the invention.

In an embodiment of a method according to one aspect of the invention, and referring to FIG. 3, the body 44 is first imaged with respect to a nuclear magnetic resonance property in at least one dimension. In the present embodiment, the dimension is along the longitudinal axis of the body 44. Imaging the NMR property in one dimension in the present embodiment includes making a first NMR measurement sequence that includes sets of RF power pulses being passed through the antenna (14 in FIG. 1), as shown generally at 46 on line A of the graph in FIG. 3. The RF power pulse sets 46 may be arranged to produce Carr Purcell Meiboom Gill (CPMG) sequences, having a first transverse (excitation) nuclear magnetization pulse and a plurality of inverting (refocusing) nuclear magnetization pulses each of which is followed by a NMR signal detection interval. Such sequences are well known to those skilled in the art. The number of spin echoes detected in each CPMG sequence may be limited, for example, to about twenty spin echoes, because for this portion of a method according to the invention, only an approximate NMR total signal amplitude is needed for the purpose of producing the one-dimensional image. Line B of the graph in FIG. 3 shows the amplitude, at curve 48, of a gradient magnetic field superimposed on the static magnetic field by passing DC through the gradient coil (20 in FIG. 1). In methods and systems according to the invention, the magnitude of the applied gradient should be substantially larger than any gradients existing in the static magnetic field. In the present embodiment, the gradient field is substantially constant amplitude and is oriented along the longitudinal axis of the chamber (16 in FIG. 1), such that the total field amplitude increases monotonically and preferably (although not necessarily) substantially linearly with respect to position along the chamber. On line C of the graph in FIG. 3 is shown an amplitude of a superimposed static magnetic field, at curve 50, applied by passing DC through the field control coil (18 in FIG. 1). As shown by curve 50, the applied static magnetic field reduces the total field amplitude such that the total static magnetic field amplitude is a selected, different amount during each CPMG sequence 46. The combination of the total selected static magnetic field amplitude, and the superimposed gradient field has the effect of localizing nuclear magnetic resonance excitation at the RF operating frequency of the system (10 in FIG. 1) to selected "slices". See slice 45 in FIG. 2 as an example. As the total static field amplitude is selectively increased for each CPMG sequence in the example of FIG. 3, (by reducing the amplitude of the superimposed static magnetic field) the axial position (x in FIG. 2) of the portion of the body (slice) subject to total static magnetic field amplitude corresponding to NMR excitation at the RF operating frequency of the system is moved axially. As will be readily appreciated by those skilled in the art, the thickness of each image slice is related to the bandwidth of the receiver (32 in FIG. 1) and the magnitude of the gradient. Using the slicing imaging sequence as shown graphically in FIG. 3, a rapid one-dimensional image of the body (44 in FIG. 2) can be made using, for example, the sum of spin echo amplitudes in each CPMG measurement sequence as a measure of the relative mass of the body component along each slice (45 in FIG. 2). Thus, an estimate of the axial endmost positions of selected body portions, such as the head 44A, or the abdomen 44B, for example, can be determined by a comparison of total NMR signal amplitude with respect to axial position, x. While other methods and systems for determining axial limits of body portions could be used, for example, optical scanning, the present invention provides a way to use the same NMR imaging apparatus to perform both the localization (by one dimensional image analysis) and the composition analysis. In the present embodiment, the coil section switch (26 in FIG. 2) can be operated to energize only portions of the antenna (14 in FIG. 2) that are disposed near the slice being investigated at any point in time. It will also be appreciated by those skilled in the art that a similar result may be obtained by superimposing the gradient field, as shown in FIG. 3, and changing the frequency of the RF magnetic field, such that NMR excitation and detection takes place at selected positions along the axis of the chamber where the RF magnetic field frequency corresponds to the total static magnetic field amplitude for which NMR excitation takes place. Determining the position of the various body portions using frequency-localized one-dimensional imaging is substantially the same as using static magnetic field amplitude adjustment to localize the imaging in the one dimension.

Figure 4:
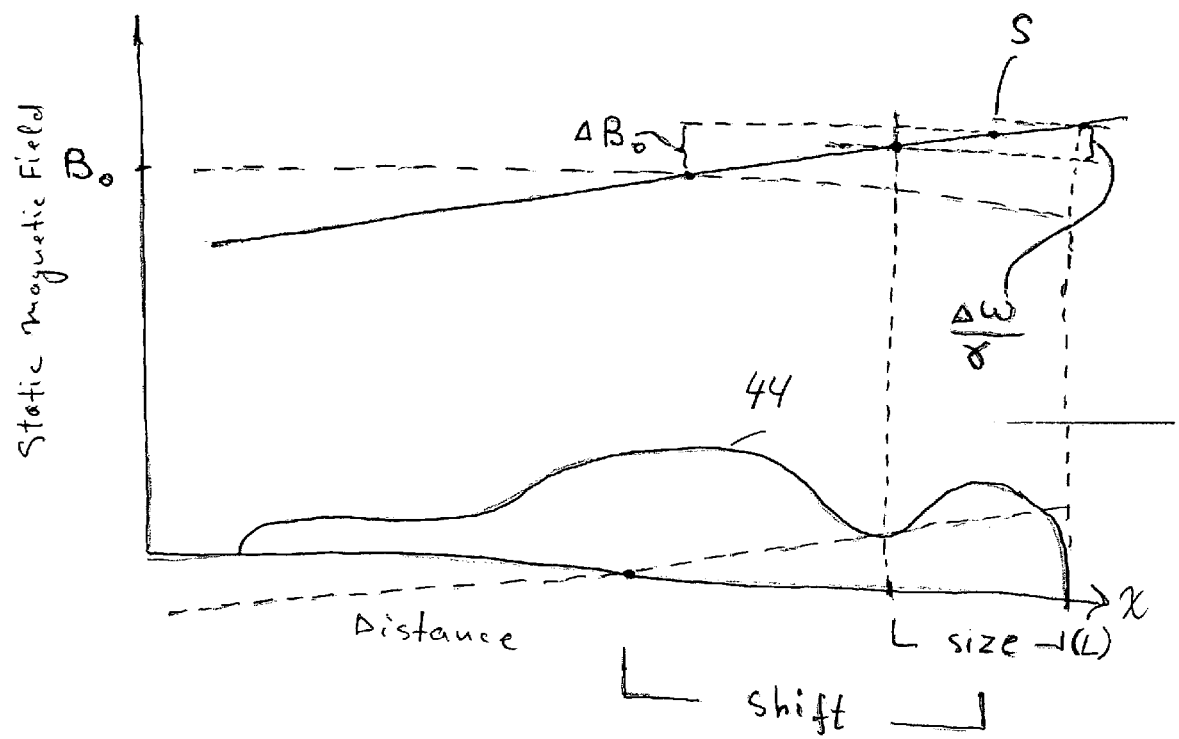
FIG. 4 shows an example localized body composition analysis technique according to the invention.

Having determined the axial position limits of a portion of the body to be analyzed, the analysis of the body portion composition proceeds as will be explained with reference to FIG. 4. The graph in FIG. 4 shows the magnetic field amplitude with respect to axial position x along the chamber (16 in FIG. 1) when the body 44 is disposed in the chamber. In this part of the measurement method according to the invention, an amount of static magnetic field adjustment (using field control coil 18 in FIG. 1) and a magnitude of gradient field (using gradient coil 20 in FIG. 1) are selected such that a center of a nuclear magnetic resonance field amplitude at the RF operating frequency of the system is disposed approximately in the center of the body portion being analyzed. Further, the amplitude of the gradient field is selected such that an axial distance (size) of the NMR region corresponds to the bandwidth of the receiver (32 in FIG. 1). Thus, NMR excitation and signal detection is substantially localized within a known, selected region along the axis of the chamber (16 in FIG. 1). Additionally, the coil section switch (26 in FIG. 2) may be used to localize RF excitation and detection to those portions of the chamber roughly corresponding to the body portion being analyzed.

The axial size L of the portion being analyzed, and its geometric center S along the axis of the chamber can be readily determined by the following expressions:

$$L = \Delta\omega/\gamma G$$

in which G is the gradient amplitude, ω is the receiver bandwidth and γ is the gyromagnetic ratio for hydrogen ($^1H$) where hydrogen nuclei are those excited for NMR analysis; and $$\Delta B_0/G = S$$

in which $B_0$ represents the magnitude of the applied adjustment to the static magnetic field. As is the case for the fast slice imaging method described previously, it is not necessary in the analysis portion of a method according to the invention for the static magnetic field to be very homogeneous, as long as the applied gradients are substantially greater than any existing gradients in the static magnetic field.

Having thus localized the portion of the body in the chamber subject to NMR excitation and signal detection, RF power pulses may be passed through the antenna (14 in FIG. 1) or selected portion thereof, and NMR signals can be detected. In the present embodiment, the localized NMR measurements can be CPMG sequences for a relatively large number of spin echoes, such that composition analysis may be performed by multicomponent exponential decay analysis such as will provide mass fractions of several components each having unique transverse and/or longitudinal nuclear magnetic relaxation times. In the present embodiment, body portion composition analysis may include determining fat tissue, lean tissue and water fractions of the body portion.

2. Body Composition Analysis by Segmenting NMR Measurements Along one Dimension of the Body into Selected Known Volumes of Investigation.

Figure 5:
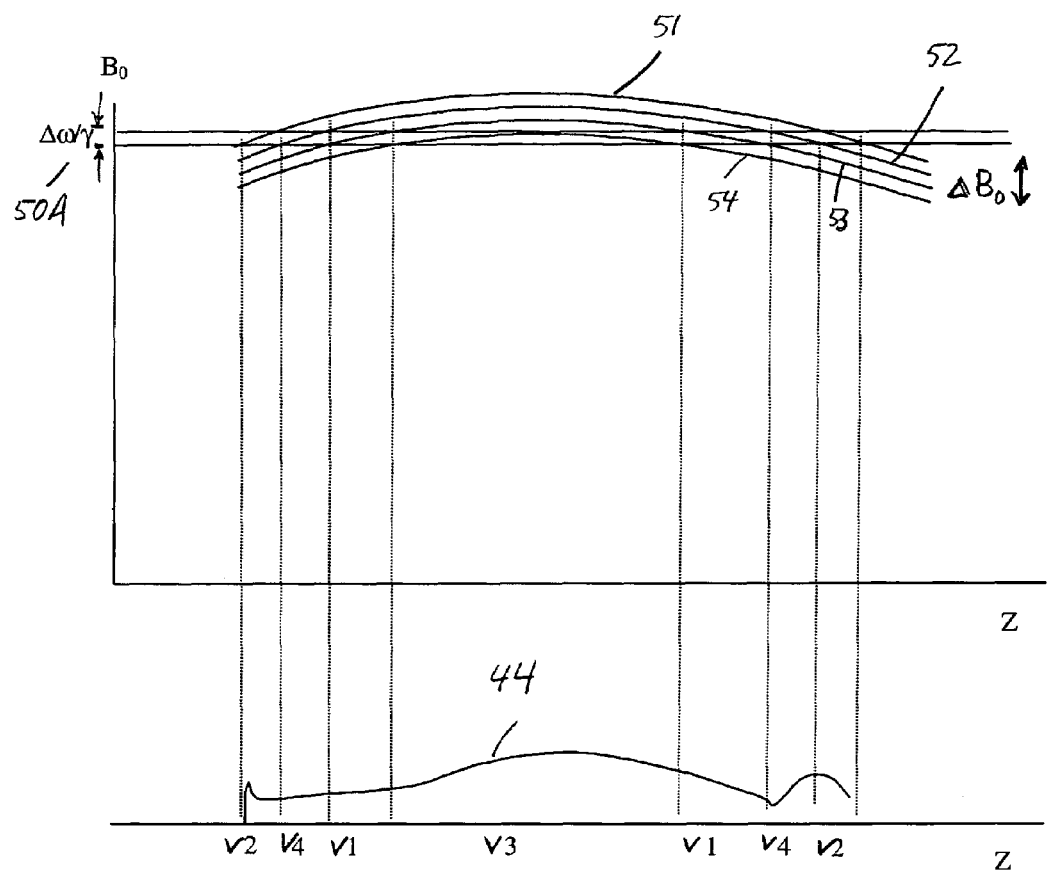
FIG. 5 shows another example localized body composition analysis technique according to the invention.

Further aspects of methods and systems according to the invention relate to body composition analysis by segmenting measurements along one dimension, preferably the longitudinal axis, of the body. One such aspect of a method and system according to the invention will now be explained with reference to FIG. 5. As will be readily appreciated by those skilled in the art, the size and cost of the magnet (12 in FIG. 1) can become very large if the body 44 being analyzed is relatively large and long. For example, a human adult may exceed 2 meters in length. The size and cost of a magnet needed to induce a substantially homogeneous static magnetic field in three dimensions along such a length can make conventional NMR analysis of body composition, using three dimensional imaging techniques, prohibitively expensive. In the present aspect of the invention, the magnet is of a size and configuration such that the static magnetic field may be somewhat inhomogeneous along the longitudinal axis of the chamber (16 in FIG. 1), while enabling whole body composition analysis to be performed. Advantageously, methods and systems according to this aspect of the invention may provide accurate, rapid whole body composition analysis using much smaller, less expensive magnets and associated NMR measurement systems. It is preferable, in methods and systems according to this aspect of the invention, that the static magnetic field induced by the magnet (12 in FIG. 1) still be substantially homogeneous in a direction perpendicular to the longitudinal axis of the body 44, and for purposes of the explanation which follows, it is assumed that the magnet (12 in FIG. 1) is configured to have a substantially homogeneous field perpendicular to the longitudinal axis of the chamber (16 in FIG. 1). In FIG. 5, a graph of static magnetic field intensity, $B_0$, with respect to position Z along the longitudinal axis of the body 44 is shown at 53. The static magnetic field distribution shown at curve 53 is such that NMR phenomena will be excited in, and thus be able to analyze composition within, a first sensitive volume portion V1 of the body 44. The exact position along the longitudinal axis of the body 44 where the sensitive volume V1 exists, and the longitudinal dimension (thickness) of volume V1 will depend on the static magnetic field amplitude distribution, the radio frequency (RF) selected for NMR excitation, and the RF magnetic field and receiver bandwidth. The curve 53 shows, as expected, some variation in static field amplitude with respect to longitudinal position Z. At the axial positions, Z, corresponding to sensitive volumes V1, the static field amplitude distribution is such that nuclear magnetic resonance excitation at the selected RF frequency, bandwidth and receiver bandwidth will occur in and be detected from sensitive volumes V1.

In the present embodiment, a relatively short CPMG measurement sequence can be performed at the selected RF frequency and static field amplitude such that analysis of body composition may be performed corresponding to the portion of the body 44 disposed within sensitive volumes V1. As in the previously described embodiments, composition analysis may include fat, water and lean tissue fractional volume determination using NMR analysis techniques known in the art.

In one embodiment according to the present aspect of the invention, different sensitive volumes along the axis of the body 44, shown at V2, V3, V4, can be selected for composition analysis by superimposing a selected amount of additional static magnetic field onto the static field induced by the magnet (12 in FIG. 1), using the field control (24 in FIG. 1) and field control coil (18 in FIG. 1). As the total static magnetic field amplitude is changed using the field control (24 in FIG. 1) and field control coil (18 in FIG. 1), the location (axial position) of the NMR excitation volume along the longitudinal axis will change correspondingly as a result of the field amplitude distribution of the magnet (12 in FIG. 1). For example, curve 54 corresponds to the static field amplitude distribution in which NMR excitation will occur in sensitive volume V3. Curve 51 corresponds to the static field amplitude distribution in which NMR excitation will occur in sensitive volumes V2. Curve 52 corresponds to the static field amplitude distribution in which NMR excitation will occur in volumes V4.

Figure 7A:
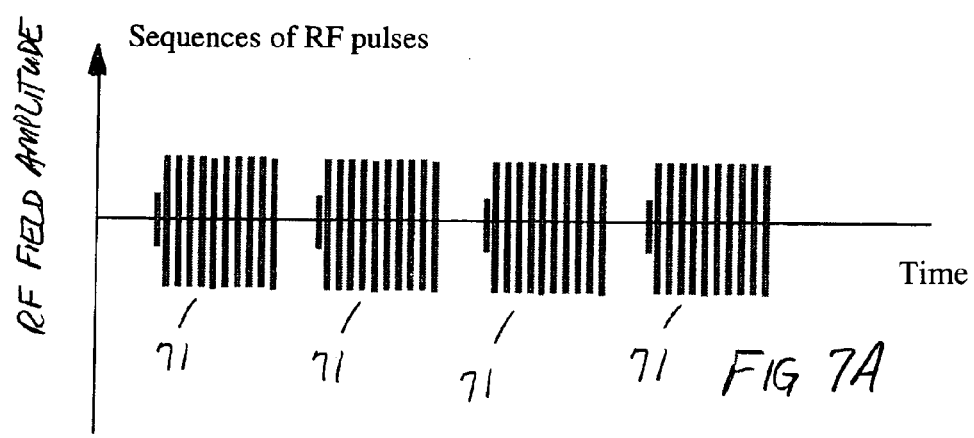
FIGS. 7A and 7B show RF magnetic field and static magnetic field amplitudes for the example localized technique shown in FIG. 5.
Figure 7B:
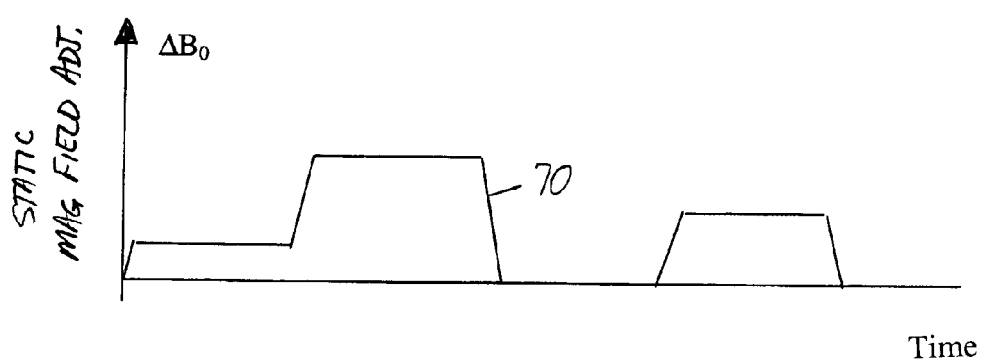

Referring to FIG. 7A, a series of RF power pulse sequences is shown as RF field amplitudes 71 at a selected frequency and bandwidth, which is shown at 50A in FIG. 5 as $\omega/\gamma$. The RF power pulses may be in the form of CPMG sequence, providing enough spin echoes to enable determining total body composition within each of the sensitive volumes being analyzed. It is well known to those skilled in the art that the CPMG pulse sequence comprises one excitation (transverse magnetization) pulse providing a nuclear magnetic spin rotation angle of about 90 degrees and a plurality of (inverting) refocusing pulse typically having spin rotation angle of substantially 180 degrees. In systems known in the art, the inverting pulses typically have the same amplitude and a duration twice that of the excitation pulse. In one embodiment according to the present invention the excitation pulse preferably has substantially the same duration as the refocusing pulses but one half the amplitude. Substantially equal width (duration) of the excitation and refocusing pulses ensures that the excitation pulse does not affect a larger volume than the refocusing pulses, because the bandwidth is substantially the same as for the excitation pulses. The bandwidth of the receiver is preferably chosen to be substantially equal to the bandwidth of the excitation and refocusing pulses. FIG. 7B shows an amount of static magnetic field adjustment, at curve 70, provided using the field control (24 in FIG. 1) and field control coil (18 in FIG. 1). In the present embodiment, the static field amplitude is preferably selected such that successive volumes analyzed are not contiguous along the longitudinal axis of the body (44 in FIG. 5). By successively analyzing non-contiguous volumes, the chance is reduced that NMR signals originating in one volume will interfere with NMR signals originating in the successively analyzed volume. Body composition analyzed form each successive volume may be summed to provide a whole body composition. In the present invention better accuracy for whole body composition measurements is achieved by making the spatial parameters of NMR excitation and detection such that there is substantially homogeneous sensitivity within each successive selected volume, and there is an abrupt change of the sensitivity to substantially zero at the boundary of the selected volume.

In one particular embodiment, the size (longitudinal dimension) of the particular sensitive volume being analyzed may be increased by increasing the bandwidth of the RF pulses used to perform NMR excitation. In one embodiment, the pulse programmer (40 in FIG. 1) can be programmed to provide shaped RF pulses having an almost rectangular frequency spectrum. This type of frequency spectrum corresponds to a "sinc" waveform of the general form y=(sin(x)/x) in the time domain. The effect of shaped pulses is explained as applied to selective excitation in magnetic resonance imaging in, P. T. Callaghan, *Principles of Nuclear Magnetic Resonance Microscopy*, Clarendon Press, Oxford, 1991. Another way to improve the bandwidth of the RF magnetic field is the use of composite RF pulses, a variety of which are explained in R. R. Ernst, et al., *Principles of Nuclear Magnetic Resonance in One and Two Dimensions*. In the case of composite pulses a regular excitation or refocusing pulse is replaced by a sequence of two, three or more pulses, each of which is characterized by its own rotation angle and phase of the RF carrier. Nuclear magnetization generated using composite pulses is much less sensitive to variations in the RF magnetic field strength, and is less sensitive to static magnetic field inhomogeneity. The expression below is an example of a refocusing composite pulse (having a nominal rotation angle of 180°) containing three sub-pulses: $(\beta)_{\pi/2} (2\beta)_0 (\beta)_{\pi/2}$, where $\beta$ is the nominal rotation angle of the excitation pulse (usually 90°); and the subscripts represent the phase of the carrier frequency in the sub-pulses.

Figure 6:
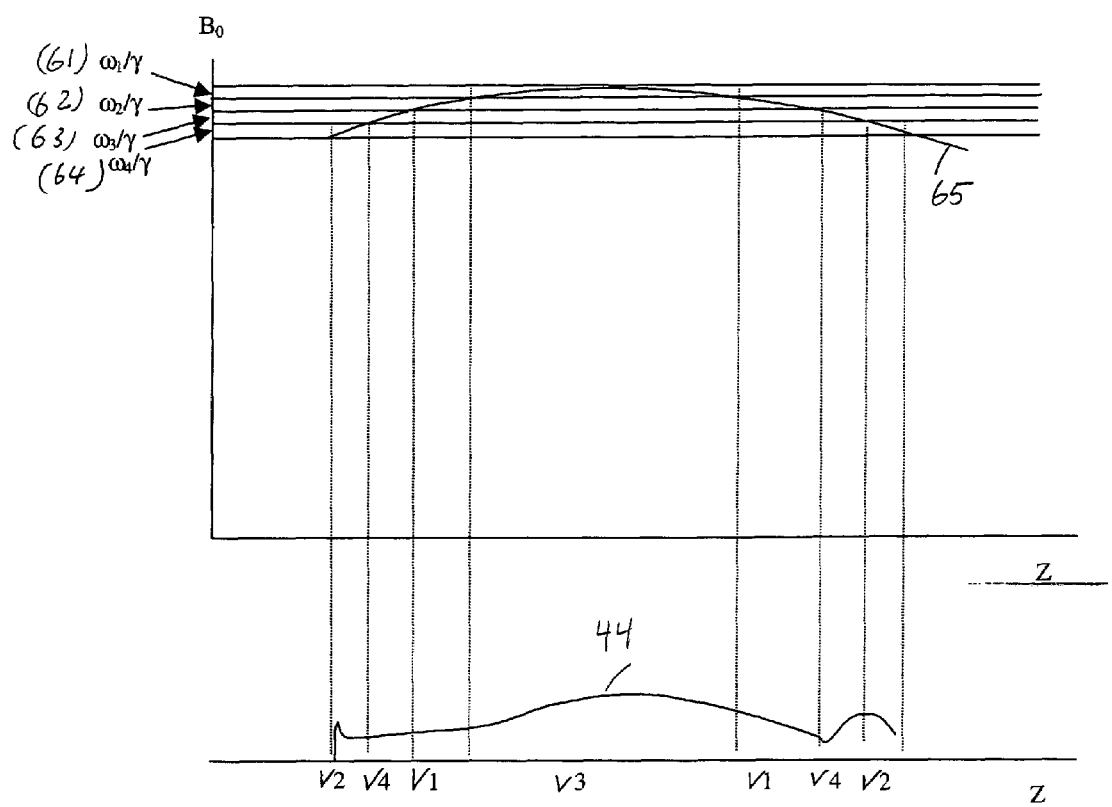
FIG. 6 shows another example localized body composition analysis technique according to the invention.

An alternative embodiment of analyzing body composition within selected volumes along the axis of the chamber can be explained with reference to FIG. 6. The curve representing static magnetic field amplitude is shown at 65. At 61, 62, 63, and 64, the RF magnetic field frequency may be selected such that NMR excitation is limited to selected volumes, such as shown at V1, V2, V3 and V4. As in the previous embodiments, it is preferable that successive volumes not be contiguous along the longitudinal axis such the interference between successively acquired NMR measurements is minimized. In some embodiments, the RF frequency may be selected by appropriate programming of the pulse programmer (40 in FIG. 1). In some embodiments, the longitudinal dimension of the sensitive volumes may be increased by increasing the bandwidth of the RF magnetic field as previously explained.

In an alternative to the embodiment previously explained with reference to FIG. 3, in one embodiment of a method according to another aspect of the invention, and once again referring to FIGS. 2 and 3, the composition of the body 44 can be analyzed in selected locations along the longitudinal axis using the following axial localization technique. In the present embodiment the technique includes making a first NMR measurement sequence that includes sets of RF power pulses being passed through the antenna (14 in FIG. 1), as shown generally at 46 on line A of the graph in FIG. 3. The RF power pulse sets 46 may be arranged to produce Carr Purcell Meiboom Gill (CPMG) sequences, having a first transverse nuclear magnetization pulse and a plurality of inverting (refocusing) nuclear magnetization pulses each of which is followed by a NMR signal detection interval. The number of spin echoes detected in each CPMG sequence may be limited, for example, to a number of spin echoes sufficient to determine body composition within each localized volume from analysis of the spin echo amplitudes.

Line B of the graph in FIG. 3 shows the amplitude, at curve 48, of a gradient magnetic field superimposed on the static magnetic field by passing DC through the gradient coil (20 in FIG. 1). In the present embodiment, the magnitude of the applied gradient field should be substantially larger than any gradients existing in the static magnetic field. In the present embodiment, the gradient field is substantially constant amplitude and is oriented along the longitudinal axis of the chamber (16 in FIG. 1), such that the total field amplitude increases monotonically with respect to position along the chamber (16 in FIG. 1). Notably, the static magnetic field need not be substantially homogeneous along the longitudinal axis of the chamber (16 in FIG. 1), but its amplitude distribution along the axis of the chamber (16 in FIG. 1) only need be known, such that the axial position of each sensitive volume ("slice") can be determined where the sum of the gradient field and static field amplitudes results in a total magnetic field amplitude corresponding to NMR excitation at the selected RF frequency. In the present embodiment, in addition to the gradient field being applied, the static magnetic field amplitude is changed using the field control (24 in FIG. 1) and field control coil (18 in FIG. 1) such that NMR excitation takes place at selected positions along the longitudinal axis of the chamber (16 in FIG. 1). On line C of the graph in FIG. 3 is shown an amplitude of a superimposed static magnetic field, at curve 50, applied by passing direct current through the field control coil (18 in FIG. 1). As can be seen in curve 50, the superimposed static magnetic field changes the total static magnetic field amplitude such that the total static magnetic field amplitude is a selected, different amount during each CPMG sequence 46. The combination of the total selected static magnetic field amplitude, and the superimposed gradient field has the effect of localizing nuclear magnetic resonance excitation at the RF operating frequency of the system (10 in FIG. 1) to selected "slices" along the axis of the chamber (16 in FIG. 1). See slice 45 in FIG. 2 as an example. As the total static field amplitude is selectively changed for each CPMG sequence, in the example of FIG. 3, the axial position (x in FIG. 2) of the portion of the body (slice) subject to total static magnetic field amplitude corresponding to NMR excitation at the RF operating frequency of the system is moved axially. As will be readily appreciated by those skilled in the art, the thickness of each slice is related to the bandwidth of the receiver (32 in FIG. 1) and the magnitude of the static magnetic field gradient at each axial position. Using the "slicing" sequence as shown graphically in FIG. 3, a rapid analysis of the body (44 in FIG. 2) can be made, for example, by analysis of spin echo amplitudes measured in each axial slice. Advantageously, a method and system according to the present embodiment minimizes the amount of RF power needed to excite NMR phenomena in the analyzed portion of the body, and reduces the degree of homogeneity of the static field induced by the magnet (12 in FIG. 1) needed to perform the composition analysis.

It will be readily appreciated by those skilled in the art that the location of any individual slice or excitation volume may be localized by changing the frequency of the RF magnetic field, while leaving the static magnetic field amplitude constant. In this localization technique, the gradient field is superimposed on the static magnetic field, just as in the preceding embodiment. However, no adjustment is made to the static field amplitude. In the present embodiment, the frequency of the RF magnetic field is changed such that NMR excitation and detection takes place within selected slice volumes along the longitudinal axis of the body. As in the preceding embodiment, the slice thickness is related to the gradient amplitude and the bandwidth of the RF receiver. Also as in the preceding embodiment, composition of the body in each slice may be determined by selected length CPMG measurement sequences localized in each slice, and analysis of the spin echo amplitudes measured in each slice.

Figure 8A:
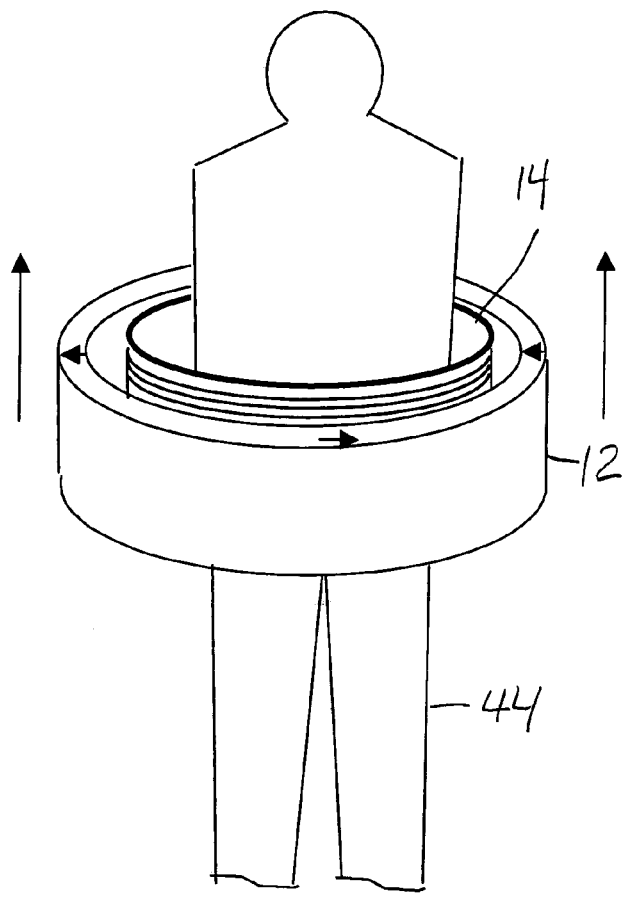
FIGS. 8A and 8B show another embodiment of a measurement technique according to the invention.
Figure 8B:
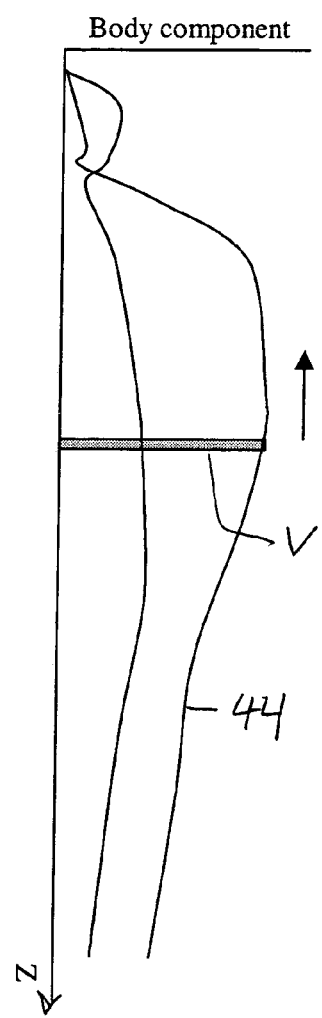

Still another embodiment of NMR body composition analysis can be explained with reference to FIGS. 8A and 8B. In FIG. 8A, the magnet 12 and the RF antenna 14 are configured such that they are smaller than a longitudinal dimension of the body 44 being analyzed. The magnet 12 and antenna 14 may be configured to move longitudinally along the body 44, or alternatively, the body 44 may be moved through the magnet 12 and antenna 14. The present embodiment may omit the field control coil (18 in FIG. 1) and the gradient control coil (20 in FIG. 1) and their associated circuitry as explained with reference to FIG. 1. The magnet 12 and the antenna 14 are configured to induce and measure, as shown in FIG. 8B, NMR phenomenal related to body composition of a known volume V disposed at a selected position along the longitudinal axis of the body 44. By moving the magnet 12 and the antenna 14, or conversely, by moving the body 44 with respect to the magnet 12 and the antenna 14, ultimately the entire body 44 can be analyzed. Systems and techniques for moving the body 44 with respect to the magnet 12 and the antenna 14 are well known in the art.

Figure 9A:
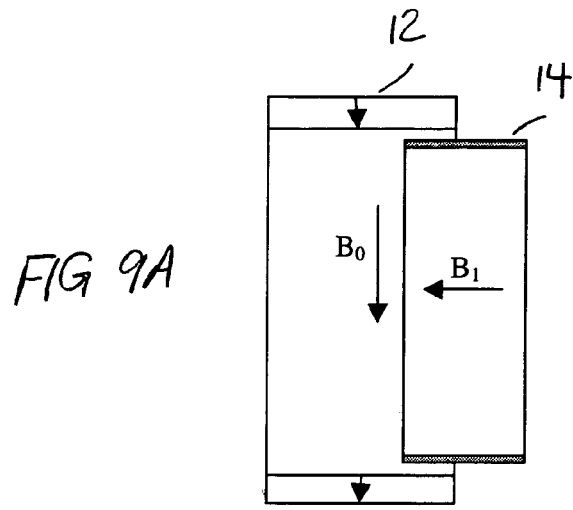
FIGS. 9A, 9B and 9C show static magnetic field distribution, RF magnetic field distribution and relative placement of an antenna with respect to a magnet for the embodiment of FIGS. 8A and 8B.
Figure 9B:
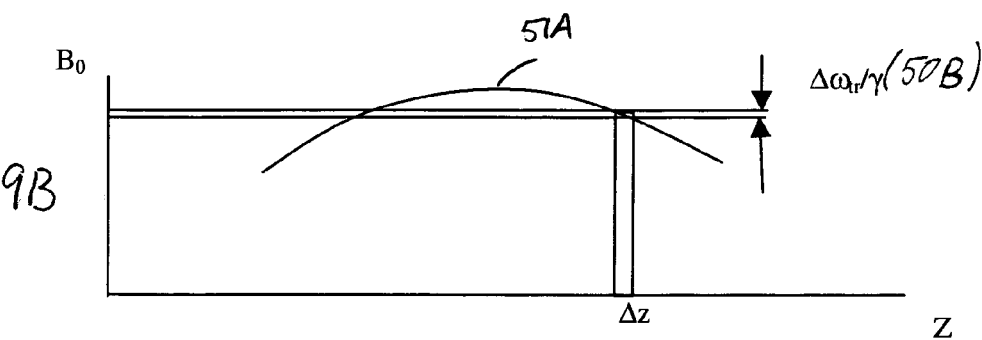
Figure 9C:
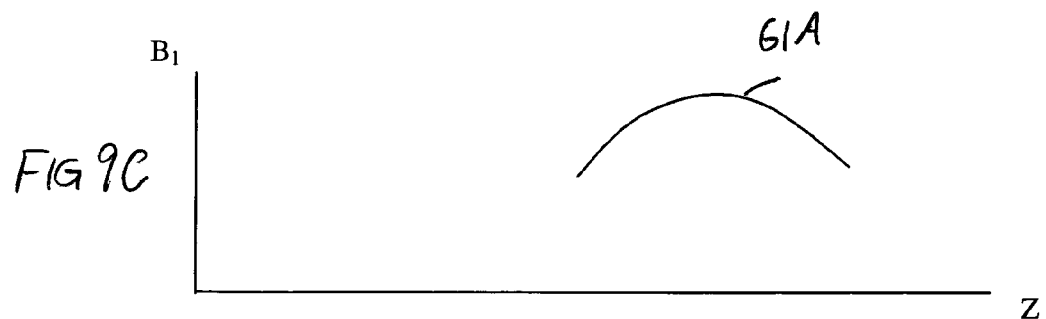

The manner in which the embodiment of FIGS. 8A and 8B can use a relatively small, inexpensive magnet can be better understood with reference to FIGS. 9A, 9B and 9C. In FIG. 9A, the magnet 12 is configured to induce a static magnetic field that is substantially homogeneous in the plane perpendicular to the axis of the body (44 in FIG. 8A). However, the static magnetic field need not be substantially homogeneous in the Z direction along the longitudinal axis. It is only necessary to know the static magnetic field distribution along the longitudinal axis. The antenna 14 should be arranged such that the RF magnetic field induced by the antenna 14 is substantially perpendicular to the static magnetic field (from the magnet 12) at the position along the longitudinal axis of the volume of investigation (V in FIG. 8B). FIG. 9B shows the static magnetic field amplitude with respect to axial position at curve 51A. The volume of investigation is indicated by Z, where the RF frequency and bandwidth, $\omega/\gamma$, indicated at 50B, correspond to the position where the static magnetic field amplitude is that necessary for NMR excitation. FIG. 9C shows that the axial position of the antenna 14 should be selected with respect to the magnet 12 such that the RF field amplitude, at curve 61A, is substantially uniform in amplitude within the axial position of the volume of investigation Z. This antenna position will provide substantially uniform NMR excitation, and by the principle of reciprocity, the sensitivity of the antenna 14 with respect to the NMR phenomena will be substantially uniform within the volume of investigation Z. As will be readily appreciated by those skilled in the art, the longitudinal dimension (thickness) of the volume of investigation will be related to the static magnetic field gradient and the RF magnetic field and receiver bandwidth within the volume of investigation. As will also be appreciated by those skilled in the art, a waiting time between successive measurements along the longitudinal axis will be related to the excitation slice (sensitive volume) thickness Z, and the speed of the relative longitudinal motion in order to avoid interference successive excitation volumes.

It should also be noted that while in the foregoing embodiments the antenna is configured to induce a substantially uniform amplitude radio frequency magnetic field within the excitation slice, it is possible to adapt use an antenna which does not produce substantially uniform radio frequency magnetic field amplitude within the excitation slice. Accurate composition analysis using such antenna configuration may be obtained by making the nuclear magnetic resonance signal sensitivity be substantially uniform in each excitation slice. In some embodiments, signal sensitivity may be made more uniform by increasing the bandwidth of the radio frequency pulses passed through the antenna. In some embodiments, signal sensitivity may be made more uniform by minimizing the spatial variation in the antenna sensitivity.

Analysis of the body composition in any of the foregoing embodiments of the invention may include whole body composition determination. Whole body composition determination is typically performed by summing the compositions determined for each slice, segment or body component determined according to any of the foregoing embodiments to obtain the composition of the entire body. It is also possible, using the various embodiments of the invention to generate or determine a body composition distribution along the body axis. As can be inferred from the description of the various embodiments, composition of each slice, segment or body component is determined in separate sequences of NMR measurements. The compositions determined from, for example, the spin echo amplitudes in each segment, component or slice can be plotted, or numerically associated with the position of the segment, component or slice to produce a body composition distribution along the axis of the body.

Figure 10:
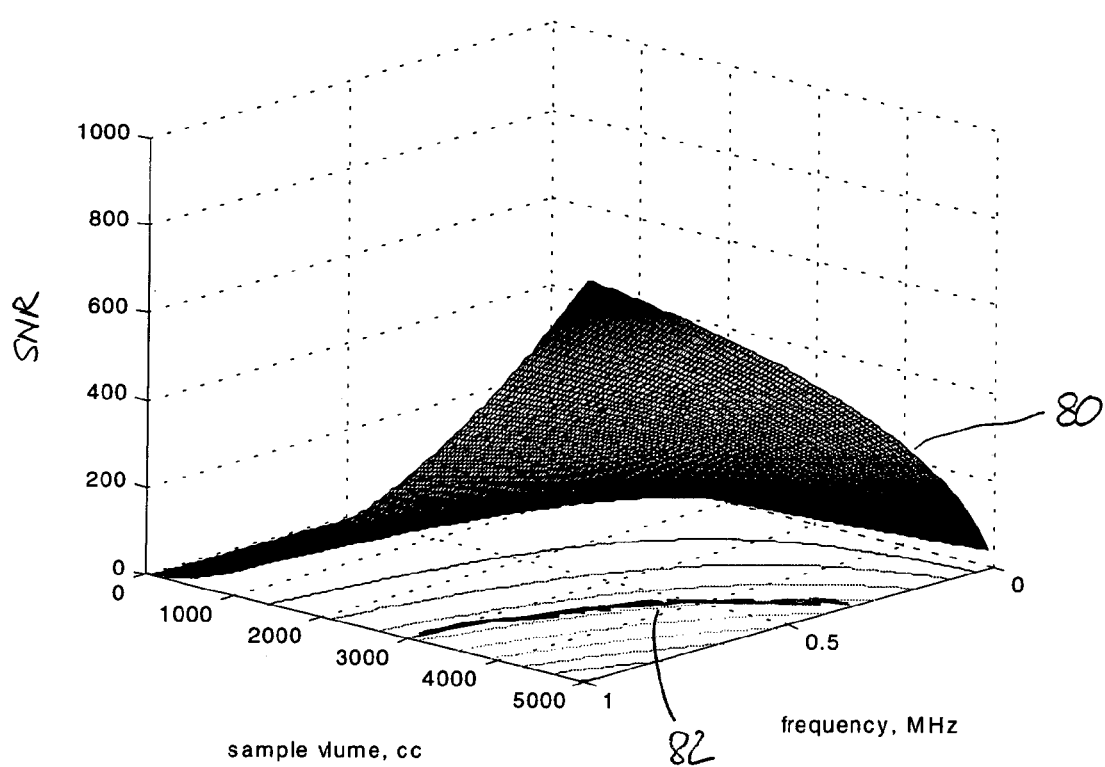
FIG. 10 shows a three dimensional graph of sample volume, RF operating frequency and SNR for selecting a minimum strength magnet.

As shown in FIG. 10, an important relationship exists between the size of the volume being analyzed (related to the slice volume, depending on the particular embodiment), and the choice of NMR operating frequency (the frequency of the RF pulses applied to the antenna). As is well known in the art, the NMR excitation frequency is proportional to the static magnetic field intensity and the gyromagnetic ratio of the nuclei being analyzed. The relationship between NMR operating frequency and the size of the volume being analyzed can be used in various embodiments to select a minimum strength static magnetic field, and corresponding NMR operating frequency, which will provide measurements having acceptable accuracy and precision. FIG. 10 shows a three-dimensional graph, at surface 80, of the signal-to-noise ratio (SNR) with respect to the sample (slice) volume and the NMR operating frequency. For a particular value of SNR, as required to perform selected duration and yet accurate NMR composition analysis measurements, there is a relationship between the minimum NMR frequency that facilitates obtaining the required accuracy with respect to the volume being analyzed (slice or volume, depending on the embodiment). The relationship between slice volume and NMR frequency for selected values of SNR is shown in FIG. 10. Curve 82 represents the minimum NMR frequency as it relates to the selected chamber volume for SNR of 100. As will be appreciated by those skilled in the art, longer duration NMR measurements sequences may be used with lower SNR. The value of SNR selected will thus be related to the speed with which NMR analysis needs to be performed on any particular type of body. Irrespective of the SNR selected, the relationship between slice volume and minimum NMR frequency can be used to minimize, for any selected slice volume, the strength of the magnet used to induce the static magnetic field. Designing NMR system with minimum NMR frequency thus provides the benefits of reducing the size, weight and cost of the magnet assembly.

Advantageously, methods and systems according to the present invention provide fast, inexpensive composition analysis of selected portions of an animal or human body without the need to anesthetize the body, overly restrict its movement, or to use large, expensive magnet systems having very high homogeneity in the static magnetic fields induced.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed is:

1. A method for analyzing composition of a body portion, comprising:

inducing a substantially homogeneous static magnetic field and a substantially uniform gradient magnetic field in an entire body, a gradient of the gradient magnetic field being along a predetermined axis of the body;

inducing a substantially homogeneous radio frequency magnetic field in the entire body while inducing the combined static and gradient magnetic fields, the radio frequency magnetic field having a frequency and a bandwidth selected to excite nuclear magnetic resonance phenomena in a segment of the body along the axis;

determining at least an amplitude of a nuclear magnetic resonance signal;

adjusting at least an amplitude of the static magnetic field and repeating the inducing the radio frequency magnetic field and determining at least the amplitude of a nuclear magnetic resonance signal from another segment of the body along the axis;

determining a portion of the body for analysis from the at least the amplitudes of the nuclear magnetic resonance signals;

selecting at least an amplitude of the static magnetic field and a gradient of the gradient magnetic field to excite nuclear magnetic resonance phenomena in the determined portion of the body, the gradient selected such that the determined portion has a selected size along the axis;

inducing a radio frequency magnetic field in the entire body;

detecting nuclear magnetic resonance signals from the determined body portion;

determining a mass of at least one constituent in the determined body portion from the detected nuclear magnetic resonance signals therefrom; and at least one of displaying and storing the determined mass.

2. The method of claim 1 wherein inducing the radio frequency magnetic field and detecting nuclear magnetic resonance signals to determine the body portion comprises performing a Carr Purcell Meiboom Gill sequence.

3. The method of claim 2 wherein the size and position of the body component are determined by a total nuclear magnetic resonance signal amplitude with respect to a position of each body portion along the axis.

4. The method of claim 1 further comprising analyzing a composition of the body portion by determining relative fractions of each of a plurality of components, each of the components having a unique transverse nuclear magnetic relaxation time.

5. The method of claim 1 further comprising analyzing a composition of the body portion by determining relative fractions of each of a plurality of components, each of the components having a unique longitudinal nuclear magnetic relaxation time.

6. The method of claim 1 wherein the inducing the radio frequency magnetic field and the detecting nuclear magnetic resonance signals are substantially localized with respect to the body portion.

7. The method of claim 1 wherein the body part is within a human patient and the mass is determined without anesthetizing, sedating and restricting movement of the human patient.

8. A system for body portion composition analysis, comprising:

a magnet for inducing a substantially homogeneous static magnetic field in an entire body;

means for inducing substantially homogeneous radio frequency magnetic field in the entire body perpendicular to the static magnetic field;

means for detecting nuclear magnetic resonance phenomena in the body;

means for applying a substantially uniform gradient magnetic field to the body having a selectable gradient along a selected axis, the means for inducing the static field and means for inducing the gradient field configured such that the static and gradient fields are polarized in the same direction; and means for selectively controlling amplitude of the static magnetic field, and means for controlling a gradient of the gradient field, the means for applying the gradient field and the means for controlling amplitude configurable to image a nuclear magnetic resonance property of the body along the selected axis at a single selected radio frequency, the means for applying the gradient field and means for controlling amplitude configurable to cause excitation of nuclear magnetic resonance phenomena in a selected full cross-section portion of the body having a selected position and size along the selected direction; and means for determining a mass of at least one constituent in the body portion from detected nuclear magnetic resonance signals.

9. The system of claim 8 further comprising means for analyzing composition of the portion of the body from detected nuclear magnetic resonance signals.

* * * * *